(12) United States Patent
Srinivas et al.

(10) Patent No.: US 7,153,806 B2
(45) Date of Patent: *Dec. 26, 2006

(54) ENCAPSULATED OXO-BRIDGED ORGANOMETALLIC CLUSTER CATALYST AND A PROCESS FOR THE PREPARATION THEREOF

(75) Inventors: Darbha Srinivas, Pune (IN); Suhas Arunkumar Chavan, Pune (IN); Paul Ratnasamy, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/924,340

(22) Filed: Aug. 23, 2004

(65) Prior Publication Data

US 2005/0181936 A1    Aug. 18, 2005

Related U.S. Application Data

(63) Continuation of application No. 09/894,997, filed on Jun. 28, 2001, now abandoned.

(51) Int. Cl.
*B01J 31/00* (2006.01)
*C07F 15/06* (2006.01)
*C07F 13/00* (2006.01)

(52) U.S. Cl. ............ 502/150; 502/153; 502/154; 502/155; 502/162; 502/167; 502/170; 546/2; 556/49

(58) Field of Classification Search ........... 502/103, 502/150, 153, 154, 155, 162, 167, 170; 546/167; 556/49
See application file for complete search history.

(56) References Cited

U.S. PATENT DOCUMENTS

| | | | |
|---|---|---|---|
| 4,414,005 A * | 11/1983 | De Bievre et al. | 95/127 |
| 4,728,455 A | 3/1988 | Rerek | |
| 4,871,790 A * | 10/1989 | Lamanna et al. | 523/333 |
| 5,167,942 A * | 12/1992 | Balkus et al. | 423/705 |
| 5,326,734 A * | 7/1994 | Vaughan | 502/84 |
| 5,416,051 A * | 5/1995 | Vaughan | 502/84 |
| 5,516,738 A * | 5/1996 | Jureller et al. | 502/155 |
| 5,840,264 A * | 11/1998 | Pinnavaia et al. | 423/277 |
| 5,922,920 A * | 7/1999 | Bond et al. | 568/342 |
| 5,981,424 A | 11/1999 | Durante et al. | |
| 6,521,789 B1 * | 2/2003 | Srinivas et al. | 562/528 |
| 6,649,791 B1 * | 11/2003 | Srinivas et al. | 562/416 |
| 6,780,810 B1 * | 8/2004 | Choudary et al. | 502/150 |
| 2003/0008770 A1 * | 1/2003 | Srinivas et al. | 502/124 |

FOREIGN PATENT DOCUMENTS

| | | |
|---|---|---|
| EP | 0694333 | 1/1996 |
| EP | 1270070 A1 * | 1/2003 |
| EP | 1270539 A1 * | 1/2003 |

OTHER PUBLICATIONS

Sabater, et al., "Chiral salen manganese complex encapsulated within zeolite Y: a heterogeneous enantioselective catalyst for the epoxidation of alkenes", Chem. Commun. 1997 1285-1286.*
Chavan, et al., "Oxidation of cyclohexane, cyclohexanone and cyclohexanol to adipic acid by a non HNO3 route over Co/Mn cluster complexes", Journal of Catalysis, 212, 39-45 (2002).*
Chavan, et al., "Selective oxidation of para-xylene to terepthalic acid by m3-oxo-bridged Co/Mn cluster complexes encapsulated in Zeolite Y", Journal of Catalysis, 204, 409-419 (2001).*
Chavan, et al., "Structure and catalytic properties of dimeric copper (II) acetato complexes encapsulated in zeolite Y", Journal of Catalysis, 192, 286-295 (2000).*
www.sciencebase.com/mar00_iss.html□□"Ship in a bottle catalysts", Elemental Discoveries, Mar. 2000, Issue 27.*
Creyghton, Edward, "Zeolites: Organic groups cling to the pores", Nature, 393, 21-22 (May 7, 1998).*
Ichikawa, Masaru, "Ship in a Bottle Catalyst Technology", Platinum Metals Rev., 2000, 44, (1), 3-14.*
Song, et al., "Improved Methanol to Olefin Catalyst with Nanocages Functionalized through Ship-in-a-bottle Synthesis from PH3", Angew. Chem. Int. Ed. 2003, 42 (8), 891-894.*
Chavan, et al. "Formation and role of cobalt and manganese cluster complexes in the oxidation of p-xylene", J. Molec. Cat. A: Chemical 161(2000) 49-64.*
Chemical Abstracts, Chavan, S.A., et al. "Formation and role of cobalt and manganese cluster complexes in the oxidation of p-xylene" 134:42462, (2000) XP-002186037.
Chemical Abstracts, Balkus, K.J., et al. "Zeolite encapsulated metal complexes" 123:297224 (1995), XP-002186038.
Chemical Abstracts, Chavan, S.A., et al. "The structural basis for the enhanced oxygenase activity of copper acetate . . . zeolites" 133:146820, (2000), XP-002186039.

(Continued)

*Primary Examiner*—Karl Group
(74) *Attorney, Agent, or Firm*—Ladas & Parry LLP

(57) ABSTRACT

The present invention relates to a novel encapsulated organometallic cluster complex catalyst and to a process for the preparation thereof. The oxo-bridged organometallic cluster complex of the invention has at least one atom of cobalt and manganese encapsulated in micro and mesoporous porous solids like aluminosilicate zeolites, aluminophosphates, carbon molecular sieves, silica and is particularly effective for oxidation of aromatic alkyl groups to the carboxyl groups in high yields.

15 Claims, No Drawings

OTHER PUBLICATIONS

Chemical Abstracts, Chavan, S.A., et al. "Structure and Catalytic Properties of Dimeric Copper (II) Acetato Complexes . . . Zeolite-Y" 133:119957, (2000), XP-002186040.

Chemical Abstracts, Sumner, C.E., et al. "Isolation of oxo-centered cobalt (III) clusters and their role in the cobalt . . . hydrocarbons" 103:152633, (1985), XP-002186041.

Chavan, S.A., et al. "Selective Oxidation of para-Xylene to Terephthalic Acid by µ3-Oxo-Bridged Co/Mn Cluster . . . Zeolite-Y" *J. of Catalysis*, vol. 204, p. 409-419, (2001).

Sabater, M.J, et al. "Chiral salen manganese complex encapsulated within zeolite Y: a heterogeneous enantioselective . . . alkenes" *Chem. Commun.*, p. 1285-1286, (1997).

* cited by examiner

ENCAPSULATED OXO-BRIDGED ORGANOMETALLIC CLUSTER CATALYST AND A PROCESS FOR THE PREPARATION THEREOF

This application is a continuation of application Ser. No. 09/894,997 filed on Jun. 28, 2001, now abandoned claims the benefit thereof and incorporates the same by reference.

FIELD OF THE INVENTION

The present invention relates to an encapsulated oxo-bridged organometallic cluster catalyst and a process for the preparation thereof. More particularly the present invention relates to a solid catalyst containing an organometallic cluster complex having the general formula $$[M_xM'_{x'}(O)(RCOO)_nL_{n'}]Y_{n''}$$

wherein M and M' are transition metal ions, x and x' are in the range of 0 to 3 with the proviso that only one of x and x' may be 0, R is selected from the group consisting of an alkyl group containing 1 to 5 carbon atoms, an aryl group with 1 to 3 benzene rings, substituted alkyl and substituted aryl group, n is in the range of 3 to 6, L is selected from the group consisting of RCOO, pyridine, nitrogen containing organic bases, $H_2O$, organic solvent or any like ligand, Y comprises a halide ion selected from the group consisting of $ClO_4^-$, $BF_4^-$, $PF_6^-$, and $BrO_3^-$ and other like ions, n' and n" are each in the range of 0 to 3. Still more particularly, it relates to the preparation of $\mu_3$-oxo-organometallic cluster catalysts inside micro and mesoporous materials like aluminosilicate zeolites, aluminophosphates, silica, carbon molecular sieves and other like materials.

These $\mu_3$-oxo-bridged organometallic cluster catalysts are active in the production of aromatic carboxylic acids.

BACKGROUND OF THE INVENTION

Aromatic carboxylic acids, like benzoic acid, phthalic acid, terephthalic acid, trimethyl benzoic acids, naphthalene dicarboxylic acids etc., are used widely as intermediates in the chemical industry and are usually prepared from the corresponding alkyl aromatic compounds by oxidation with air in the presence of liquid phase, homogeneous catalysts like cobalt acetate, manganese acetate etc. U.S. Pat. No. 2,833,816 issued to Mid Century Corporation in 1958 discloses the preparation of terephthalic acid by the oxidation of para-xylene by air in acetic acid solvent, at around 200° C. and 200 psig pressure, in the presence of homogeneous, liquid phase catalysts comprising of cobalt, manganese and bromine. U.S. Pat. Nos. 5,693,856, 3,562,318A; 5,760,288; 6,160,159; 4,329,493; 4,593,122; 4,827,025; 4,835,307; 5,087,741; 5,112,992; and EP 0 754,673 A disclose various modifications and improvements of the process of U.S. Pat. No. 2,833,816 for the manufacture of terephthalic and many other aromatic carboxylic acids. Comprehensive reviews of the oxidation of alkyl aromatic compounds to aromatic carboxylic acids are available in Suresh et al, Industrial Engineering Chemistry Research, volume 39, pages 3958–3997, year 2000 and W. Partenheimer, Catalysis Today, volume 23, pages 69–158, year 1995. Phthalic acid is manufactured by the aerial oxidation of ortho-xylene in the vapor phase over vanadia-based catalysts.

Prior art methods for the manufacture of aromatic carboxylic acids using homogeneous liquid phase processes suffer from several disadvantages. The homogeneous catalyst used is not easily separable from the products thereby limiting the reusability of the catalysts. Prior art methods also use corrosive bromide promoters requiring the use of expensive titanium steel thereby rendering the process itself more expensive. Another disadvantage of prior art methods is that acetic acid is oxidised to CO and carbon dioxide. It is therefore important to modify presently used homogeneous, liquid phase processes for the manufacture of aromatic carboxylic acids.

Some of the improvements and modifications that are contemplated include: (1) replacement of homogeneous liquid phase catalysts by solid heterogeneous catalysts; (2) replacement of corrosive bromide promoters by non-corrosive compounds; (3) elimination or reduction of the significant acetic acid oxidation to CO and carbon dioxide (5–10 wt. % of the carboxylic acid); and (4) lowering the concentration of intermediates which are difficult to remove from the final aromatic carboxylic acid product, in the reaction product.

4-carboxy benzaldehyde is a typical example of an intermediate which necessitates elaborate hydrogenation and recrystallisation procedures in order to manufacture purified terephthalic acid required for the polyester industry. It is believed that the reduction in the oxidation of acetic acid to carbon dioxide and CO can be achieved by the use of more efficient radical promoters thereby allowing oxidizer temperatures to be lowered without reducing reaction rates.

Replacement of homogeneous catalyst system by a heterogeneous, solid catalyst system in the production of high purity aromatic carboxylic acids is desirable to facilitate easy separation of the catalyst (i.e., metal ions) from the products and for reusability of the catalyst system.

Jacob et al in the journal Applied Catalysis A: General, volume 182, year 1999, pages 91–96 described the aerial oxidation of para-xylene over zeolite-encapsulated salen, saltin and salcyhexen complexes of cobalt or manganese in the absence of added halogen promoters and using tertiary butyl hydroperoxide, instead of bromide ions, as the initiator at low temperatures. While significant conversion levels of para-xylene (up to 50–60%) were attained the main product was para-toluic acid. The yields of terephthalic acid were negligible. It was claimed that the feasibility of using a solid, non-Br-containing catalyst in the absence of any solvent including acetic acid for the para-xylene oxidation to toluic acid, (which is the first stage in the oxidation of para-xylene to terephthalic acid) was established.

Chavan et al in the Journal of Molecular Catalysis A: Chemical, volume 161, year 2000, pages 49–64 observed the formation of oxo-bridged cobalt/manganese cluster complexes in the reaction mixture and these complexes were attributed as the actual catalysts for the production of aromatic carboxylic acids.

U.S. Pat. Nos. 5,849,652; 5,603,914; 5,489,424; 5,167, 942, 5,767,320 and 5,932,773 disclose monomeric metal complexes encapsulated in molecular sieves. However, there is no reference to encapsulated oxo-bridged organometallic cluster complexes in prior art.

In the investigations leading to the present invention, it was found that when complexes of cobalt, manganese, nickel, zirconium or any of their combinations were supported or encapsulated or grafted in solid supports, the yields of the aromatic carboxylic acids were always low in accord with the findings of Jacob et al published earlier and mentioned herein above.

OBJECTS OF THE INVENTION

The main object of the present invention is to provide a novel encapsulated oxo-bridged organometallic cluster complex catalyst useful for the manufacture of aromatic carboxylic acids.

It is another object of the invention to provide a process for the preparation of novel encapsulated oxo-bridged organometallic cluster complex catalyst useful for the manufacture of aromatic carboxylic acids.

It is a further object of the invention to provide a novel encapsulated oxo-bridged organometallic cluster complex catalyst useful for the manufacture of aromatic carboxylic acids that provides high yield in use while being easily separable from the product stream.

It is yet another object of the invention to provide a novel encapsulated oxo-bridged organometallic cluster complex catalyst useful for the manufacture of aromatic carboxylic acids that renders the process of preparation of the aromatic carboxylic acids more economical and environmentally safe.

SUMMARY OF THE INVENTION

The present invention relates to the preparation of solid catalysts wherein the oxo-bridged organometallic cluster complex of at least one atom of cobalt and manganese is encapsulated in micro and mesoporous porous solids like aluminosilicate zeolites, aluminophosphates, carbon molecular sieves, silica. The solid oxidation catalysts have been found to be particularly effective for oxidation of aromatic alkyl groups to the carboxyl groups in high yields.

Accordingly, the present invention provides an encapsulated organometallic cluster complex catalyst wherein the organometallic cluster is of the general formula, $$[M_xM'_{x'}(O)(RCOO)_nL_{n'}]Y_{n''}$$

wherein M and M' are transition metal ions, x and x' are in the range of 0 to 3 with the proviso that only one of x and x' may be 0, R is selected from the group consisting of an alkyl group containing 1 to 5 carbon atoms, an aryl group with 1 to 3 benzene rings, substituted alkyl and substituted aryl group, n is in the range of 3 to 6, L is selected from the group consisting of RCOO, pyridine, nitrogen containing organic bases, $H_2O$, organic solvent or any like ligand, Y comprises a halide ion selected from the group consisting of $ClO_4^-$, $BF_4^-$, $PF_6^-$ and $BrO_3^-$ and other like ion, n' and n'' are each in the range of 0 to 3, said complex being encapsulated in a porous material.

In one embodiment of the invention, the transition metal ions are selected from the group consisting of Co, Mn and a mixture thereof.

In another embodiment of the invention, the catalyst of the invention comprises $CoMn_2(O)(CH_3COO)_6$, $Co_2Mn(O)(CH_3COO)_6$, $CoMn_2(O)(CH_3COO)_y(pyridine)_z$ and $Co_2Mn(O)(CH_3COO)_y(pyridine)_z$, wherein y+z=9.

In another embodiment of the invention, the porous material encapsulant comprises micro and mesoporous materials selected from aluminosilicate zeolites, aluminophosphates, silica and carbon molecular sieves.

The present invention also relates to a process for the preparation of the encapsulated organometallic cluster complex having general formula, $$[M_xM'_{x'}(O)(RCOO)_nL_{n'}]Y_{n''}$$

wherein M and M' are transition metal ions, x and x' are each in the range of 0 to 3 with the proviso that only one of x and x' may be 0, R is selected from the group consisting of an alkyl group containing 1 to 5 carbon atoms, an aryl group with 1 to 3 benzene rings, substituted alkyl and substituted aryl group, n is in the range of 3 to 6, L is selected from the group consisting of RCOO, pyridine, nitrogen containing organic bases, $H_2O$, organic solvent or any like ligand, Y comprises a halide ion selected from the group consisting of $ClO_4^-$, $BF_4^-$, $PF_6^-$ and $BrO_3^-$ and other like ion, n' and n'' are each in the range of 0 to 3, said process comprising interacting a zeolite HY with a mixture of solutions of sources of transition metal ions at a temperature in the range of 298 K to 358 K under constant stirring to obtain a solid product, washing and drying the solid product thoroughly at 390 to 410 K, and then adding to it a mixture of an acid, pyridine, salt of alkali metal and water, under constant agitation and in a dynamic aerobic environment for 2 to 4 h at 298 K and separating and drying the encapsulated complex at 298 K under vacuum to obtain the encapsulated oxo-bridged organometallic cluster catalyst.

In one embodiment of the invention, the transition metal ions are selected from cobalt and manganese ions.

In a further embodiment, the manganese ion source is selected from the group consisting of manganese acetate, manganese chloride and manganese nitrate.

In a more preferred embodiment of the invention, the manganese ion source is manganese acetate.

In another embodiment, the source of cobalt ions is selected from the group consisting of cobalt acetate, cobalt chloride and cobalt nitrate.

In a more preferred embodiment of the invention, the cobalt ion source is cobalt acetate.

In yet another embodiment, the alkali metal salt is selected from the group consisting of sodium bromide, sodium chloride, potassium bromide, potassium chloride and potassium iodide.

In a more preferred embodiment of the invention, the alkali metal salt is sodium bromide.

DETAILED DESCRIPTION OF THE INVENTION

It is an unique feature of the present invention that when the solid catalyst contains certain organometallic, cluster complexes of cobalt and manganese wherein each molecule of the cluster complex contains both cobalt and manganese, then their activity in the oxidation of alkyl aromatic compounds to aromatic carboxylic acids is enhanced significantly. The novel solid catalysts of the invention retain all the advantages of the homogeneous catalysts, such as high yields of the desired aromatic carboxylic acids (in the range of 96 to 98% weight) and are at the same time easily separated from the reaction products by simple filtration processes. This avoids the tedious process of catalyst recovery characteristic of prior art processes, and also eliminates the presence of toxic elements such as cobalt, manganese and nickel in the waste effluent from the process. Processes utilizing these novel solid catalysts are, hence, environmentally more beneficial.

Representative of the organometallic cluster complexes of cobalt and manganese of the present invention are $CoMn_2(O)(CH_3COO)_6$, $Co_2Mn(O)(CH_3COO)_6$, $CoMn_2(O)(CH_3COO)_y(pyridine)_z$, $Co_2Mn(O)(CH_3COO)_y(pyridine)_z$, where y+z=9, etc. It was also found that the organic ligands in the above mentioned organometallic cluster complex, namely the acetate and pyridine ligands, can be replaced by other suitable organic moieties. The critical active site ensemble responsible for the high yields of aromatic carboxylic acids in the oxidation of the alkyl aromatic compounds was the heterometallic cluster complex containing both cobalt and manganese. While the exact origin of this enhancement effect is not known in detail, it is believed that multimetallic clusters of transition metal ions are better able to activate dioxygen, $O_2$, than monometallic and monomeric ions. The common prevalence of such heteronuclear, multimetallic clusters in the $O_2$ activating enzymatic oxygenase catalyst systems supports such a suggestion. Processes for the manufacture of aromatic carboxylic acids using solid catalysts with high, almost complete, conversion of the alkyl aromatic compound and high yields of the aromatic carboxylic acid are continually sought.

Characteristic features of some catalysts prepared according to the invention are presented in Table 1 below:

TABLE 1

Characterization data of solid cobalt/manganese cluster complexes

| Sl.No. | Catalyst system | FT-IR (nujol) | UV-vis | ESR |
|---|---|---|---|---|
| 1 | $CoMn_2(O)(CH_3COO)_6(pyridine)_3$ in zeolite Y | 2924, 1624, 1458, 1221, 680 (acetato) 1545, 1489, 790 (pyridine) | Intense band at 254 nm | Signal at g = 2.023 |
| 2 | $Co_3(O)(CH_3COO)_6(pyridine)_3$ in zeolite Y | 2924, 1635, 1463, 1221, 681 (acetato) 1553, 1421, 790 (pyridine) | Intense band at 254 nm and weak band at 345 nm | Broad signal at g = 2.220, at 298K which disappears at 77K |
| 3 | $Mn_3(O)(CH_3COO)_6(pyridine)_3$ in zeolite Y | 2924, 1624, 1489, 1340, 680 (acetato) 1545, 1458, 790 (pyridine) | Intense band at 254 nm | Signal at g = 2.036 with partially resolved hyperfine coupling |

The present invention features the application of a solid catalyst containing organometallic cluster complex of cobalt and manganese in the oxidation of the alkyl aromatic compound to the aromatic carboxylic acid in the presence of an oxygen containing gas. The separation of the solid crystals of the aromatic carboxylic acid from the reaction product and isolating from the solid crystals of aromatic carboxylic acid, an aromatic carboxylic acid having a purity greater than 99% by weight form no part of the invention.

The catalyst of the invention is useful in the preparation of aromatic carboxylic acids. The preparation of aromatic carboxylic acids using the catalyst of the invention is described in our copending application Ser. No. 09/912,456, now U.S. Pat. No 6,649,791 (NF 267/2001).

This invention is illustrated by the following examples, which are illustrative only, and should not be construed to limit the scope of the present invention.

EXAMPLE-1

This example illustrates the preparation of zeolite-Y-encapsulated $CoMn_2(O)(CH_3COO)_6(pyridine)_3$ complex designated as catalyst system (1). Mixed metal Co—Mn(II) exchanged zeolite-HY was prepared by ion-exchange method, in which zeolite HY (7 g) was interacted with 4.3 g of $Mn(CH_3COO)_2.4H_2O$ and 1.43 g of $Co(CH_3COO)_2.4H_2O$ dissolved in 100 ml distilled water at 60° C. with constant stirring. The solid product was then washed thoroughly with water (500 ml) and dried at 100° C. CoMnY (1.5 g) was taken in 15 ml glacial acetic acid and to this was added pyridine (3 ml), NaBr (0.5 g) and aq. $H_2O_2$ (50%, 10 ml) and distilled water (5 ml). The reaction mixture was stirred while passing air, for 2 h, at 25° C. The brown solid zeolite (CoMn-cluster complex encapsulated in zeolite-Y; was then filtered and dried at 25° C. under vacuum.

EXAMPLE-2

This example illustrates the preparation of zeolite-Y-encapsulated $CO_3O)(CH_3COO)_6(pyridine)_3$ complex designated as catalyst system (2). Co(II) exchanged zeolite-HY was prepared by the ion-exchange method, in which zeolite HY(7 g) was interacted with 4.3 g of $Co(CH_3COO)_2.4H_2O$ dissolved in 100 ml distilled water at 60° C. with constant stirring. The solid product was then washed thoroughly with water (500 ml) and dried at 100° C. CoY, thus obtained, was used in the preparation of catalyst system 2. In a typical preparation of catalyst system (2), CoY(1.5 g) was taken in 15 ml glacial acetic acid and to it was added pyridine (3 ml), NaBr (0.5 g), aq. $H_2O_2$ (50%, 10 ml) and distilled water (5 ml). The reaction mixture was stirred while passing air, for 2 h, at 25° C. The brown solid zeolite ($CO_3$ cluster encapsulated in zeolite-Y; catalyst system 2) was then filtered and dried at 25° C. under vacuum.

EXAMPLE-3

This example illustrates the preparation of zeolite-Y-encapsulated $Mn_3(O)(CH_3COO)_6(pyridine)_3$ complex designated as catalyst system (3). Mn(II) exchanged zeolite-HY was prepared by ion-exchange method, in which zeolite HY (7 g) was interacted with 4.3 g of $Mn(CH_3COO)_2.4H_2O$ dissolved in 100 ml distilled water at 60° C. with constant stirring. The solid product was then washed thoroughly with water (500 ml) and dried at 100° C. MnY, thus obtained, was used in the preparation of catalyst system 3. In a typical preparation of catalyst system (3), MnY(1.5 g) was taken in glacial acetic acid (15 ml) and to it was added pyridine (3 ml), NaBr (0.5 g) and aq. $H_2O_2$ (50%, 10 ml) and distilled water (5 ml). The reaction mixture was stirred while passing air, for 2 h, at 25° C. The brown solid zeolite ($Mn_3$ cluster encapsulated in zeolite-Y; catalyst system 3) was then filtered and dried at 25° C. under vacuum.

EXAMPLE 4

This example illustrates the preparation of zeolite-Y-encapsulated $CoMn_2(O)(CH_3COO)_6$ complex designated as catalyst system 4. Mixed metal Co—Mn(II) exchanged zeolite HY (CoMnY) was prepared by ion exchange method as described in Example 1. CoMnY (1.5 g) was taken in 15 ml glacial acetic acid and to this NaBr (0.5 g) and aq. $H_2O_2$ (50%, 10 ml) and distilled water (5 ml) was added. The reaction mixture was stirred while passing air, for 2 hours at 25° C. The brown solid zeolite (CoMn) cluster complex encapsulated in zeolite-Y was then filtered and dried at 90° C.

EXAMPLE 5

This example illustrates the preparation of zeolite-Y-encapsulated $Co_3(O)(CH_3COO)_6$ complex designated as catalyst system 5. Co(II) exchanged zeolite HY (CoMnY) was prepared by ion exchange method as described in Example 2. CoY thus obtained was used in the preparation of catalyst system 5. In a typical preparation of catalyst system 5, CoY(1.5 g) was taken in 15 ml glacial acetic acid and to this NaBr (0.5 g) and aq. $H_2O_2$ (50%, 10 ml) and distilled water (5 ml) was added. The reaction mixture was stirred while passing air, for 2 hours at 25° C. The brown solid zeolite (catalyst system 5) was then filtered and dried at 90° C.

EXAMPLE 6

This example illustrates the preparation of zeolite-Y-encapsulated $Mn_3(O)(CH_3COO)_6$ complex designated as catalyst system 6. Mn(II) exchanged zeolite HY (CoMnY) was prepared by ion exchange method as described in Example 3. MnY thus obtained was used in the preparation of catalyst system 6. In a typical preparation of catalyst system 6 MnY(1.5 g) was taken in 15 ml glacial acetic acid and to this NaBr (0.5 g) and aq. $H_2O_2$ (50%, 10 ml) and distilled water (5 ml) was added. The reaction mixture was stirred while passing air, for 2 hours at 25° C. The brown solid zeolite (catalyst system 6) was then filtered and dried at 90° C.

ADVANTAGES OF THE INVENTION

1. The catalyst of the invention results in the retention of the advantages of using liquid phase homogeneous catalysts such as high yield of the product while being easily separable and reusable.
2. Another advantage of the catalyst of the invention is that the manufacture of aromatic carboxylic acids is rendered environmentally safe due to the absence of toxic ions of cobalt, manganese and nickel in the waste effluent.
3. A further advantage of the catalyst of the invention is that the process of manufacture of aromatic carboxylic acids using the catalyst is rendered more economical since the catalyst can be easily separated and reused as well as due to the absence of toxic ions in the waste effluent which otherwise require expensive treatment technology.

We claim:

1. An encapsulated organometallic cluster complex catalyst wherein the organometallic cluster is of formula $[MM'_2(\mu_3-O)(RCOO)_mL_m']L'_n$, wherein M and M' are 3d or mid to late transition metal ions, R is selected from the group consisting of alkyl containing 1 to 5 carbon atoms, aryl, substituted alkyl and substituted aryl group; m is in the range of from 3 to 6, L is selected from the group consisting of RCOO, pyridine, nitrogen-containing organic bases, $H_2O$, and organic solvents; L' is a halide ion or halide containing ion and m' and n are in the range of 0 to 3, said complex being encapsulated in a porous material.

2. The encapsulated organometallic cluster complex catalyst as claimed in claim 1 wherein M and M' are selected from the group consisting of Co or Mn.

3. The encapsulated organometallic cluster complex catalyst as claimed in claim 1 wherein the catalyst is selected from the group consisting of $CoMn_2(\mu_3-O)(CH_3COO)_6$, $Co_2Mn(\mu_3-O)(CH_3COO)_6$, $CoMn_2(\mu_3-O)(CH_3COO)_6(pyridine)_3$, and $Co_2Mn(\mu_3-O)(CH_3COO)_6(pyridine)_3$.

4. The encapsulated organometallic cluster complex catalyst as claimed in claim 1 wherein the porous material comprises micro and mesoporous materials selected from group consisting of aluminosilicate zeolites, aluminophosphates, silica and carbon molecular sieves.

5. A process for the preparation of the encapsulated organometallic cluster complex of formula, $[MM'_2(\mu_3-O)(RCOO)_mL_m']L'_n$, wherein M and M' are 3d or mid to late transition metal ions R is selected from the group consisting of alkyl containing 1 to 5 carbon atoms, aryl substituted alkyl or substituted aryl group, m is in range of from 3 to 6, L is selected from the group consisting of RCOO, pyridine, nitrogen containing organic bases, $H_2O$, and organic solvents, L' is a halide ion or halide containing ion and m' and n are each in the range of 0 to 3, said process comprising interacting an encapsulant with a mixture of solutions of sources of transition metal ions at a temperature in the range of 298° K to 358° K under constant stirring to obtain a solid product, washing and drying the solid product thoroughly at 390 to 410° K, and then adding to it an organic carboxylic acid, pyridine, salt of alkali metal and water, under constant agitation and pumping oxygen or air into the mixture for 2 to 4 h at 298° K and separating and drying the encapsulated complex at 298° K under vacuum to obtain the encapsulated oxo-bridged organometallic cluster catalyst.

6. The process as claimed in claim 5 wherein the transition metal ions used are selected from cobalt and manganese ions.

7. The process as claimed in claim 6 wherein the manganese ion source used is selected from the group consisting of manganese acetate, manganese chloride and manganese nitrate.

8. The process as claimed in claim 7 wherein the manganese ion source used is manganese acetate.

9. The process as claimed in claim 6 wherein the source of cobalt ions used is selected from the group consisting of cobalt acetate, cobalt chloride and cobalt nitrate.

10. The process as claimed in claim 9 wherein the cobalt ion source used is cobalt acetate.

11. The process as claimed in claim 5 wherein the alkali metal salt used is selected from the group consisting of sodium bromide, sodium chloride, potassium bromide, potassium chloride and potassium iodide.

12. The process as claimed in claim 11 wherein the alkali metal salt used is sodium bromide.

13. The process as claimed in claim 5 wherein the, porous encapsulant used comprises micro and mesoporous materials selected from the group consisting of aluminosilicate zeolites, aluminophosphates, silica and carbon molecular sieves.

14. The process as claimed in claim 5 wherein the acid used is glacial acetic acid.

15. The process as claimed in claim 5 wherein L' is selected from the group consisting of $ClO_4^-$, $BF_4^-$, $PF_6^-$, and $BrO_3^-$.

* * * * *